United States Patent [19]

Nates

[11] Patent Number: 5,123,840
[45] Date of Patent: Jun. 23, 1992

[54] SURGICAL APPARATUS

[76] Inventor: Colin Nates, 47 Erlswold Road, Saxonwold, Johannesburg, South Africa, 2196

[21] Appl. No.: 697,799

[22] Filed: May 9, 1991

[30] Foreign Application Priority Data

May 14, 1990 [ZA] South Africa .................. 90/3645

[51] Int. Cl.⁵ .................. A61C 17/06; A61M 17/14; A61M 1/00
[52] U.S. Cl. .................. 433/95; 433/91; 433/96; 604/313; 604/902
[58] Field of Search .................. 604/313–316, 604/322, 326, 902; 433/91, 99, 95, 96, 99

[56] References Cited

U.S. PATENT DOCUMENTS

| D. 298,461 | 11/1988 | Manno . | |
|---|---|---|---|
| 2,531,730 | 11/1950 | Henderson . | |
| 3,610,242 | 2/1969 | Sheridan . | |
| 3,828,780 | 8/1974 | Morrison, Jr. | 604/902 |
| 3,881,254 | 5/1975 | Epstein | 433/96 |
| 3,964,484 | 6/1976 | Reynolds . | |
| 4,430,073 | 2/1984 | Bemis . | |
| 4,468,217 | 8/1984 | Kuzmick . | |
| 4,536,180 | 8/1985 | Johnson . | |
| 4,813,926 | 3/1989 | Kerwin . | |
| 4,878,900 | 11/1989 | Sundt . | |
| 4,883,426 | 11/1989 | Ferrer . | |
| 4,886,492 | 12/1989 | Brooke . | |

FOREIGN PATENT DOCUMENTS 1566561 12/1969 Fed. Rep. of Germany .

Primary Examiner—Randy C. Shay
Assistant Examiner—A. P. Zuttarelli
Attorney, Agent, or Firm—Charles Berman

[57] ABSTRACT

A suction device is disclosed comprising a molded plastic handle having a suction bore therethrough and a spigot for connection to the hospital suction source. The device further comprises a probe having a suction passage therethrough and terminating in a suction tip. At its proximal end the probe is formed with a male thread which threadedly engages in internal threads provided at an enlarged entrance portion of the handle. The proximal end of the probe terminates in an end member which fits within a reception bore located between the front bore and the suction bore of the handle. The dimensions of the end member are such that there is an annular space between the reception bore and the end member and this space connects through an opening through the suction bore. The handle has a controllable suction port whereby the suction at the tip can be controlled. This port opens into the annular space downstream of the connection between the opening and the suction bore.

Various modifications including modifications for use with flexible catheters are also described.

19 Claims, 4 Drawing Sheets

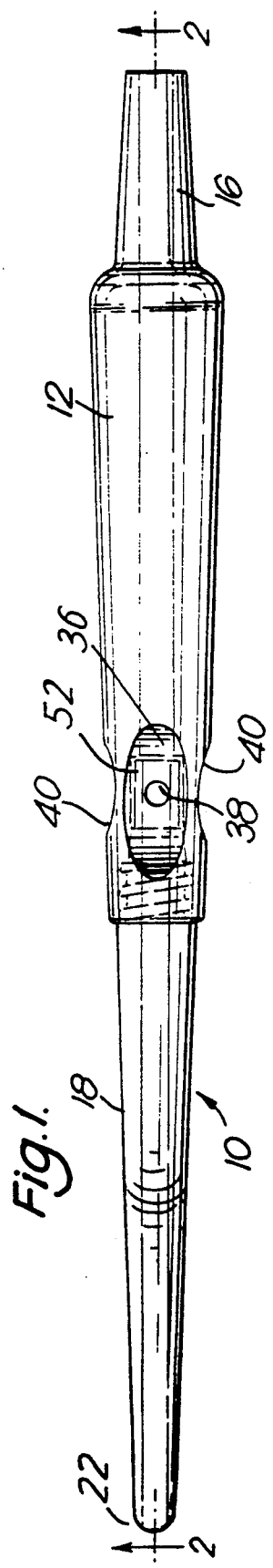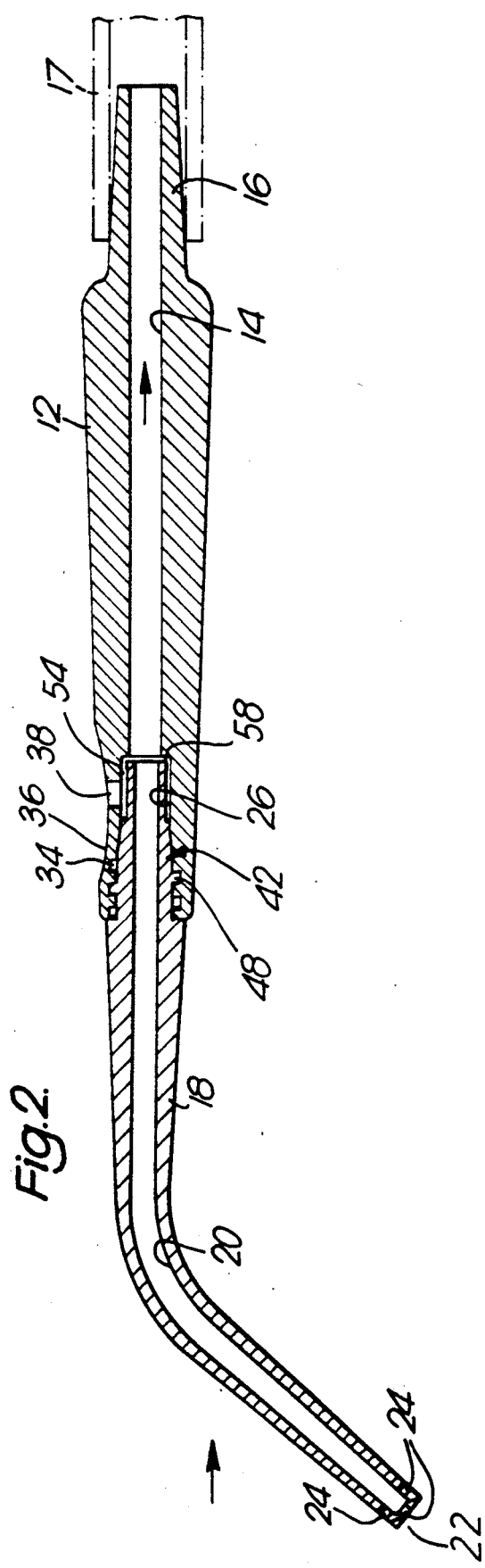
Fig.1.
Fig.2.

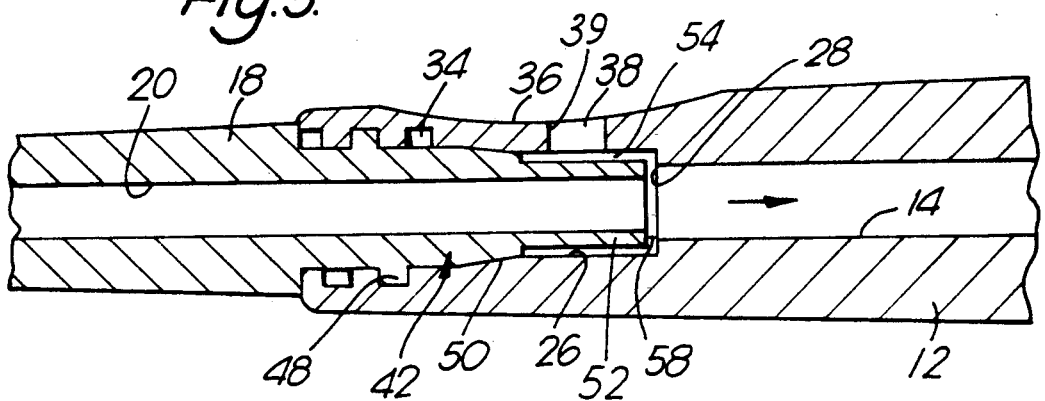
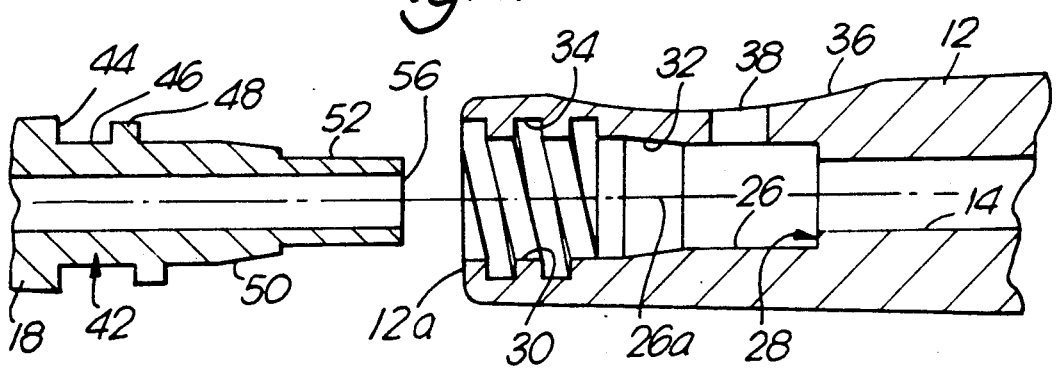
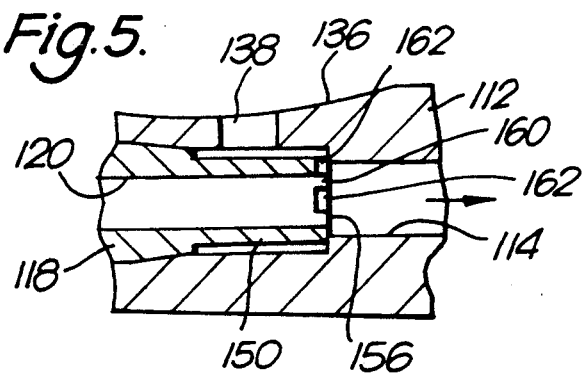

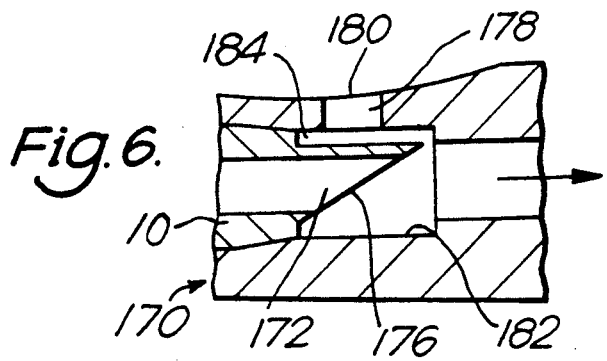
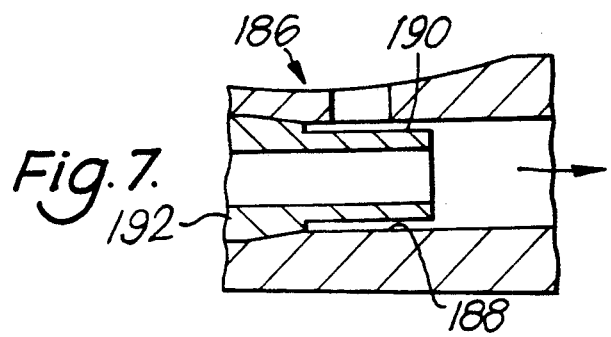
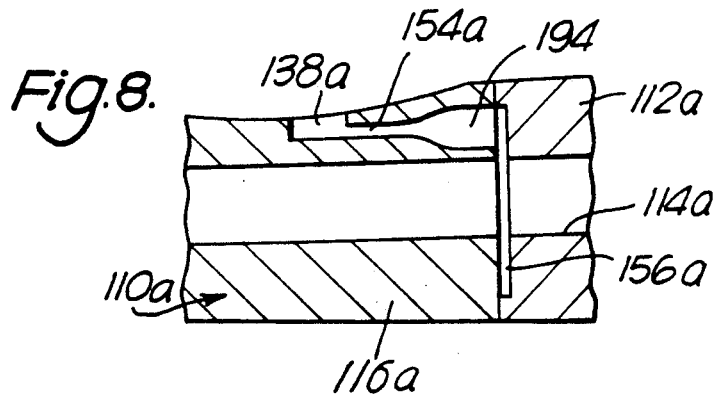
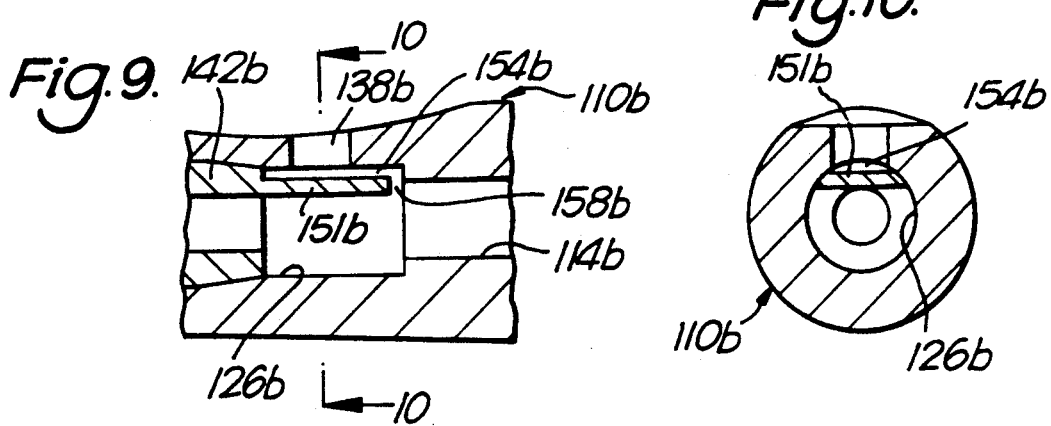

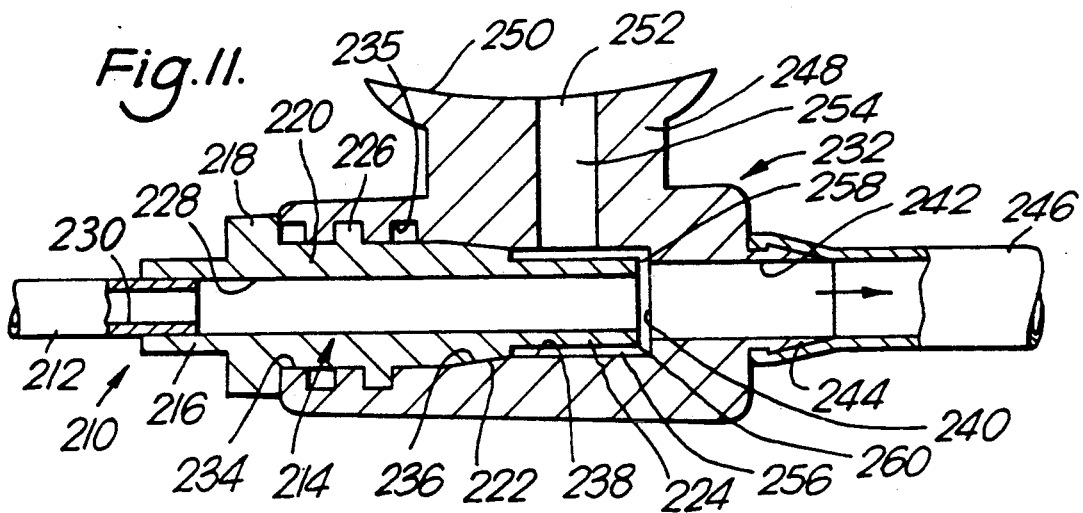
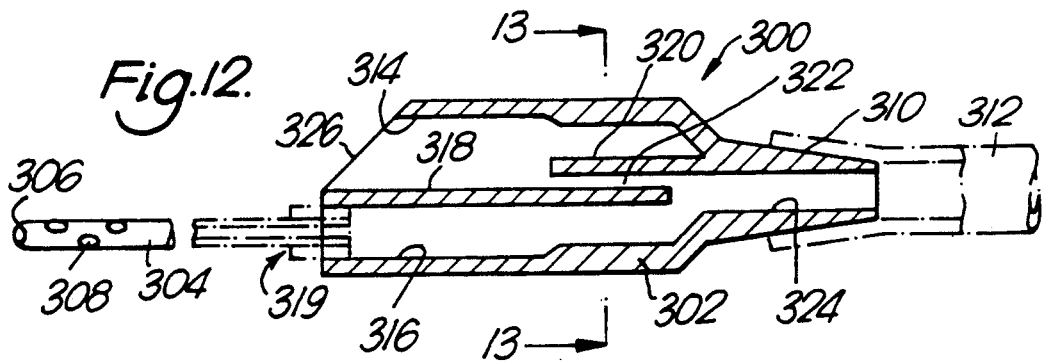
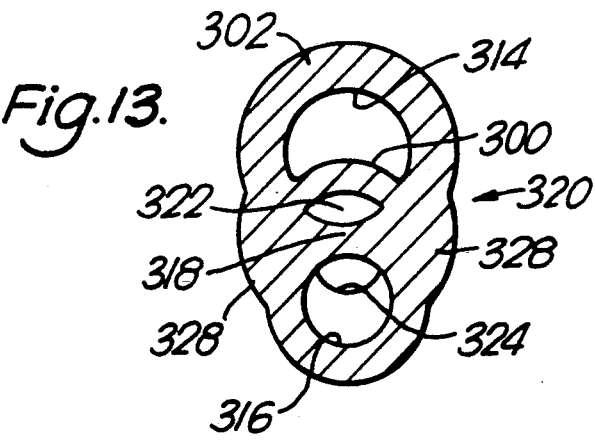

SURGICAL APPARATUS

This invention relates to suction devices and in particular such devices for medical, surgical or denial use.

BACKGROUND TO THE INVENTION

Suction devices are used for medical, surgical or dental use to remove foreign matter, fluid, blood, pus, mucous, polyps, bone particles, necrotic and cancerous matter and the like (all of which are hereinafter referred to as "waste matter"). Such suction devices are normally provided in two types via a suction nozzle comprising a rigid nozzle or a suction catheter comprising an elongated flexible catheter which can be inserted into the body as desired. The nozzle or catheter is normally connected to a suction source via an intermediate member which is connected by connection means to a flexible tube that is connected to the suction source, the connection means being normally in the form of a hollow spigot. In the suction nozzle the intermediate member may comprise a handle that may be integral with the probe.

In order that the suction can be controlled, a suction port may be provided in the intermediate member leading to the suction passage therethrough and the medical personnel operating the suction device, by obturating the suction port to a greater or lesser extent, can vary the suction at the tip of the probe.

BRIEF SUMMARY OF THE INVENTION

A controllable suction device of the invention includes a conduit leading to the suction port which conduit has one dimension that is very small i.e. of the order of 3 mm or less and preferably about 1 mm. Thus the surface tension of the waste matter will inhibit the movement of the waste matter along this conduit. The suction port will thus be protected by this conduit against the movement of waste matter to the suction port which will not be fouled by the waste matter. The conduit may have its other dimensions being quite large so that its flow area is adequate to permit sufficient air flow therethrough when the suction port is open so that there will be no or very little suction at the tip of the suction member. The conduit preferably connects to the suction passage downstream of its connection to the suction port i.e. when the suction port is open there will be air movement in the conduit in the same direction as the movement in the suction passage through the intermediate member. The conduit is preferably annular or part annular in shape.

The suction member is preferably separate from the intermediate member and preferably has a hollow spigot that fits within a reception bore in the intermediate member in such a way that the conduit is formed between the spigot and the bore, the conduit preferably being of annular cross-section. The reception bore may form part of the suction passage through the intermediate member. However the reception bore is conveniently of larger diameter than the suction passage, there being connection opening means between the conduit and the suction passage which opening means also has one dimension that is very small.

Thus an object of the present invention is to provide an improved suction device.

It is another object of the invention to provide a controllable suction device in which the suction port is protected against being fouled by waste matter being removed by the suction device.

It is a further object of this invention to provide a controllable suction nozzle wherein the probe is made separately from the handle and wherein the probe is provided with a spigot entering a reception bore in the handle, there being an annular or part annular conduit being formed between the spigot and the handle which prevents waste matter moving to the suction port.

It is yet a further object of the invention to provide a controllable suction device of the invention wherein the air moving from the suction port to the suction passage changes direction at least once and preferably two or three times.

Other objects, advantages and features of the present invention will become apparant from the following specification when taken in conjunction with the accompanying drawings.

BRIEF DESCRIPTION OF DRAWINGS

FIG. 1 is a plan of a controllable suction nozzle of the invention,

FIG. 2 is a section on line 2—2 of FIG. 1,

FIG. 3 is an enlarged detail of FIG. 2,

FIG. 4 is a view similar to FIG. 3 showing the parts in the exploded condition,

FIGS. 5, 6, 7, 8 and 9 are respectively views similar to FIG. 3 of modified suction nozzles of the invention, FIG. 10 is a section on line 10—10 of FIG. 9, FIG. 11 is a view similar to FIG. 3 of a suction catheter of the invention,, FIG. 12 is a similar view of another suction catther or the invention and FIG. 13 is a section on line 13—13 of FIG. 12.

DESCRIPTION OF THE CURRENTLY PREFERRED EMBODIMENT OF THE INVENTION

Referring now to FIGS. 1 to 4, there is shown a controllable suction nozzle 10 of the invention. The nozzle 10 comprises a hollow handle 12 having a suction bore 14 running along its length. At its rear end, the handle 12 has an integral spigot 16 formed thereon through which the suction bore 14 passes. This spigot 16 is generally frusto-conical in shape so as to be able to be received within a flexible suction tube (indicated in chain lines at 17) connected to a hospital's suction apparatus. At its front end, the handle 12 is connected to a hollow elongated rigid probe 18 having a suction passage 20 therethrough. At its forward or distal end, the probe 18 ends in a tip 22 with suitable suction openings 24 leading into the passage 20.

The handle 12 comprises an injection moulded ABS (acrilonitrile-butadiene-styrene) member containing colouring matter to make it opaque. The probe 18 is an injection moulded, substantially transparent acrylic member. The precise materials to be used will be apparant to any moulder skilled in the art. I have found that these parts engage and disengage easily and smoothly.

The front end of the handle 12 has an enlarged reception bore 26 (best shown in FIGS. 4 and 5) that is coaxial with the suction bore 14 and has a base 28 lying in a plane radial to the axis 26a of the reception bore. The diameter of the bore 26 is 10 mm. The bore 26 leads to an enlarged entrance section 30 to which it is connected by a frusto-conical part 32. The entrance section 30 has internal square section threads 34 formed therein. Above the bore 26 there is a shallow finger depression 36 formed in the outer surface of the handle. A four millimeter diameter port 38 at the end of a radial passage 39 is provided at the lowest portion of the finger depression. Finger grip depressions 40 are provided on either side of depression 36.

The proximal or rear end of the probe 18 is provided with a spigot 42, there being a radial shoulder 44 between the probe 18 and the spigot. The spigot 42 has a short externally threaded cylindrical portion 46 which has a square section thread 48 formed thereon to fit threadedly into the threads 34 in the reception bore 26. The thread 48 extends through 540° (five hundred and forty degrees).

The spigot 42 has a frusto-conical section 50 beyond the threaded portion 48 which is complementary to the portion 32 of the bore 26 and lies flush thereagainst to limit the inward movement of the spigot 42 into the bore 26 and also to seal thereagainst. The end of the section 50 is stepped down to a cylindrical end portion 52 of reduced external diameter which is two millimeters smaller than the diameter of the bore 26. The end portion 52 lies in spaced co-axial relationship within the reception bore 26 so that there is an annular space or conduit 54 between the end 50 and the bore 26. The end face 56 of the spigot 42 is located about one millimeter short of the shoulder 28 between the reception bore 26 and the suction bore 14 and closer to the rear end of the bore 14. Thus there is a cylindrical opening 58 between the annular space 54 and the bore 14 and the port 38 is in pneumatic contact with the suction bore 14 through the annular space 54 and the opening 58. It will be noted that this latter opening 58 is downstream of the join of the radial bore 39 and the annular space 54. It will further be noted that the cross-sectional area of the annular space 54 is quite substantial but that the narrowest dimension of the space, i.e. its radial width is small.

In this embodiment the cross-sectional area of the annular space 54 is 28 square millimeters shown at 28 and the radial width is one millimeter. Similarly the cross-sectional area of the opening 58 (which is cylindrical in shape) is also substantial (13 mm²) while the narrowest dimension, i.e. the axial length of the opening (1 mm), is small. The axis of the port 38 joins the annular space 54 five millimeters behind the end face 56 of the spigot 42.

The probe 18 is inserted into the handle 12 by placing the spigot 42 into the bore 26 with the probe 18 located at a position 180° from its normal working position. The threads 48 engage in the female threads 34 and the probe 18 is rotated through 540° (i.e. one and a half turns) until it reaches its desired operating position. Further movement of the spigot is prevented by engagement of the frusto-conical surfaces 50 and 32 and by the shoulder 44 of the probe 18 butting against the front end 12a of the handle.

When suction is applied to the suction nozzle, air is drawn into suction passage 14 both from the nozzle tip and the suction port 38. When the suction port 38 is open there will be little or no suction at the nozzle tip. As the suction port 38 is obturated to a greater degree by the anaesthetist's finger, the suction at the tip will be increased and of course when the suction port 38 is wholly obturated, the full suction will be applied at the nozzle tip. The controllable suction nozzle 10 can be manipulated in conventional manner by an anaesthetist into the mouth or pharynx of a patient so that the suction can be applied to matter to be removed therefrom. It can also be used to suck body fluids from the abdomen or other body cavity of a patient who is being operated upon. Because the suction can be controlled by the anaesthetist as described above, the chance of damage to tissue underlying the waste material being caused by the suction can be minimised or totally avoided.

It will be noted that the direction of air movement changes at right angles from the suction port 38 to along the conduit 54, then at right angles through the opening 58 and then again at right angles into the suction bore 14.

It has been found that the suction nozzle 10 operates effectively and well. Furthermore because the connection between the annular conduit 54 to the passage 14 is upstream of opening 56, waste material will not migrate to the port 38. It is believed that because of the enlargement of the flow passage at the opening 58, increased suction will be caused—through the conduit 54. This will provide inter alia improved clearing of conduit 54 when the nozzle is connected to suction and the suction port 38 is at least partially open. It is also believed that the annular conduit 54 also serves as a plenum chamber which also serves to prevent movement of the waste material to the suction port 38. Indeed the air flow through the conduit 58 will move such matter away from the suction port 38 which will normally if not always remain clean in use. Thus the medical personnel's finger will not be contaminated by such waste matter. It has also been found that when the nozzle 10 is hung up, as some times occurs in the theatre or recovery room, waste matter in the nozzle which will tend to move down the suction bore 14 will not pass through the gap 58 but will instead take the path of least resistance and pass down the passage 20. The possibility of the waste matter entering the annular conduit 54 which is extremely small or minimal is reduced still further in the FIG. 5 embodiment to be described below.

Furthermore, because the suction nozzle 10 is formed in two parts, the mold in which the parts are made can be of significantly less size, as can be the mold insert(s), and consequently is less costly than the moulds for conventional suction nozzles. These nozzles 10 thus can be disposable. In addition, the probes can be of varying shapes and sizes and tip configurations can be mounted on a handle of one shape, thus reducing still further the costs of manufacture while permitting the anaesthetist considerable scope in the choice of probe to be used.

It has further been found, surprisingly, that the suction noise of the nozzle 10 is much lower than that of conventional suction nozzles. This noise can barely be heard against the noises in the operating theatre and does not cause irritation and distraction in the operating theatre. It is thought that the end member 50 on the spigot 42 serves as a baffle which reduces noise as aforesaid.

DESCRIPTION OF SOME MODIFIED SUCTION NOZZLES OF THE INVENTION

The modified nozzle shown in FIG. 5 is generally similar to the embodiment of FIGS. 1 to 4 (and wherein the reference numbers for identical parts are the same with the addition of 100 to the numbers) save that the end 156 of the spigot 142 is provided with castellations 160 which engage the base 128 of the reception bore 126. Thus the opening 158 is formed by a plurality of ports 162 between the castellations 160.

Reference is now made to FIG. 6. The nozzle 170 therein shown is substantially identical to the nozzle 10 save that the end member 172 has its front face 176 cut on an incline. The passage 178 from the suction port 180 enters the reception bore 182 upstream of the end of the longest portion of the end member which is located directly below the suction port 180 i.e. it enters into a narrow conduit 184 prior to being connected to the reception bore.

In the embodiment of FIG. 7, the nozzle 186 has a reception bore 188 is of the same diameter as, and is a continuation of, the suction passage. Thus the annular conduit 190 surrounding the end part 192 of the spigot enters into the suction passage through an annular opening without a further change of direction of the air passing therethrough.

In FIG. 8, the suction nozzle 110a has a suction port 138a that is formed in the proximal end of the probe 116a which is at this end of relative great wall thickness. The nozzle 138a connects to a narrow conduit 154a of a few millimeters length and a minimum cross-sectional dimension of one millimeter formed in the wall of the probe 116a. This conduit 154a leads to a plenum chamber 194 of somewhat greater diameter that is also formed in the nozzle wall and that opens into an annular connecting port 156a formed by an annular recess in the front face of the handle 112a. This port 156a connects with the suction bore 114a. The connection between the probe 116a and the handle 112a may be effected as desired and is not illustrated herein.

The suction nozzle 110a operates in the same way as the embodiments described above. The provision of the plenum chamber 194 and the small conduit 154a prevents waste matter migrating to the suction port 138a.

The suction nozzle 110b illustrated in FIGS. 9 and 10 is generally similar to the suction nozzle 10 save that the spigot does not have an annular end 50. Instead the spigot 142b is provided with a chordal shield 151b that seals against the walls of the reception bore 126b (as best shown in FIG. 10) to leave an elongated passage 154b whose radial dimension is small. This passage 154b connects with the suction port 114b through a narrow opening 158b that is located downstream of the suction port 138b.

The suction nozzle 110b operates in the same manner as the embodiments described above. The provision of the small conduit 154b prevents waste matter migrating to the suction port 138b and contaminating the aneasthetist's finger.

DESCRIPTION OF TWO MODIFIED SUCTION CATHETERS OF THE INVENTION

Referring now to FIG. 11, there is shown a detail of a suction catheter device 210 of the invention. The device 210 comprises a flexible catheter 212 that extends any desired length and terminates in a suction tip (not shown) at its distal end. A connector or union 214 is attached to the proximal end of the catheter. The union 214 includes a front spigot 216, a flange 218 leading to a cylindrical body 220 having a frustoconical section 222 that terminates in a smaller end spigot 224. Male threads 226 are provided on the body 220. A suction passage 228 connected to the bore 230 of the catheter 212 extends through the union 214. The union 214 fits into the front end of an intermediate member 232 which has an entrance bore 234 provided with internal threads 235 and leading via a frusto-conical part 236 to a reception bore 238. The reception bore 238 has a flat base 240 into which opens a suction passage 242 of smaller dimensions. The intermediate member 232 terminates in a spigot 244 which fits into the theatre suction pipe 246. A radial boss 248 extends from the central portion of the intermediate member 232 and has at its upper end a finger rest 250. A suction port 252 is provided in the finger rest leading to a short bore 254 that extends radially of and into the reception bore 238.

As mentioned above, the union 214 fits the front end of the intermediate member. The body 220 fits the entrance bore 234 with the male threads 226 engaging the internal threads 235. The frusto-conical section 222 butts and seals against the frusto-conical part 236 of the bore and the end spigot 224 is coaxially received within the reception bore 238 in such a way that there is an annular conduit 256 therebetween. The end face 258 of the end spigot 224 is spaced slightly from the base 240 of the reception bore 238. Thus there is a cylindrical opening 260 between the conduit 256 and the suction passage 242. The bore 254 enters the conduit 256 upstream of the opening 260.

Reference is now made to FIGS. 12 and 13 wherein is shown a suction catheter 300 including an intermediate member or handle 302 and a flexible catheter 304 having a tip 306 at its distal end formed with suitable ports 308.

The handle 302 has a spigot 310 at its proximal end for connection to a tube 312 leading to the hospital suction device. Internally the handle 302 has upper and lower passages 314 and 316 separated by a longitudinally extending cross-piece 318 that terminates somewhat short of the spigot 310. The passage 316 receives a plastic union 319 in which the distal end of the catheter 304 is sealingly received.

The distal end of the passage 314 has an inclined face 326 to provide a suction port that an anaesthetist can control with his finger to control the suction at the tip 306 of the catheter 304.

A transverse somewhat arcuate shield 320 is formed integrally with the handle 302 and overlies the distal end of the cross-piece forming therewith a narrow conduit 322 that has a small vertical dimension and that extends in the direction of the handle for a few (about eight) millimeters. This conduit 322 connects together the passage 314 with the passage 316 and the suction bore 324 of the spigot 310 downstream from the suction port. It will be noted too that the passage 314 extends beyond the connection between the passage 314 and the conduit 322.

Extra material is provided at either side of the handle (302) at 328 for improved rigidity.

In this embodiment as in the previously described embodiments, waste matter will not foul the suction port. Also the suction noises emitted by this device are minimal.

GENERAL

All the embodiments described are inexpensive and can be disposable. No moving parts are required for the operation and control of the suction device. Because of the controlled amount of rotation of the probe as described above (via one and a half turns) and the disposition of the threads, the precise and repeatable angular positioning of the probe relative to the handle in the suction nozzles above described can be effected.

The invention is not limited to the precise constructional details hereinbefore described and illustrated. For example, the handle may be of any desired shape and size and the probe can be of any desired shape and size. The tip of the probe can be shaped or configured as desired. The connection between the probe and the handle can be varied as desired and indeed the probe can be permanently secured to the handle. Some or all of the finger different materials with the probe being preferably transparent. Although the materials are preferably plastics materials, one or both of the parts can comprise metal. The arrangement with a catheter need not incorporate the boss and finger plate, the suction port being formed directly in the intermediate member. The nozzle may of course be used by medical personnel not only in the operating theatre but also in the recovery room or wheresoever medical draining or suction is required.

The various dimensions given apply to the currently apparatus of the invention. However these dimensions may vary as required save that the narrow dimension of the conduit (54 etc) should be sufficient for the waste member to form a miniscus thereacross i.e. normally up to about 3 mm and preferably about 1 mm. The transverse shield in the catheter device 210 can be straight.

The suctions devices can be put to other uses with or without such suitable modification for such purposes. Thus they may be used for sucking, removing or transfering matter in a controlled manner in industrial or laboratory conditions without the operator having his finger contaminated thereby.

The invention now being fully described, it will be apparaent to one of ordinary skill in the art that many changes and modifications can be made thereto without departing from the spirit or scope of the invention as set forth in the following claims.

What is claimed is:

1. A suction device comprising
   (a) a suction member having distal and proximal ends, an internal suction passage terminating at a suction tip at the distal end thereof;
   (b) an intermediate member having a connection part for connection to a source of suction, a suction bore that is connectable to the suction passage to form a suction line through the device and a controllable suction port; and
   (c) an annular conduit which is narrow in one dimension and which connects the suction port to the suction line, and
   (d) wherein said suction member has an end part entering the suction bore and defining therewith said conduit.

2. A device as claimed in claim 1 wherein said suction port is connected to said conduit upstream of its connection with said suction line.

3. A device as claimed in claim 1 wherein said suction member comprises a rigid suction probe and said intermediate member comprises a rigid handle.

4. A device as claimed in claim 1 wherein said suction member comprises a flexible catheter connected to said intermediate member.

5. A device as claimed in claim 4 further comprising a union connecting said flexible catheter to said intermediate member.

6. A suction device comprising:
   (i) a suction member having distal and proximal ends, a tip at said distal end, and at said proximal end, a connection device including an end member, there being a suction passage through said suction member;
   (ii) an intermediate member having a suction bore therethrough, and connecting means connectable to a source of vacuum pressure so that the suction bore is subject to said vacuum pressure, the suction bore having a reception portion and a remainder portion, said reception portion receiving therein said end member so that there is an annular conduit formed therearound, which conduit connects with said remainder portion of said suction bore; and
   (iii) a controllable suction port leading from outside the intermediate member to the conduit and connecting with the conduit upstream of the connection between said conduit and said remainder portion of said suction bore.

7. A device as claimed in claim 6 in which said suction bore has an enlargement at its distal end forming said reception bore portion in which said end member is received.

8. A suction device as claimed in claim 7
   in which there is a surface at the junction between said reception bore portion and said remainder portion of said suction bore,
   in which said end member terminates short of said surface, and
   in which the said opening is formed between said surface and said distal end of said end member.

9. A suction device as claimed in claim 8 in which said surface extends in a plane perpendicular to the axis of said reception bore.

10. A device as claimed in claim 6 in which said end part comprises a shield that butts against said suction bore to define therewith said conduit.

11. A device as claimed in claim 10 wherein said suction port is connected to said conduit upstream of its connection with the suction bore.

12. A device as claimed in claim 6 further comprising a finger rest raised from said intermediate member, said suction bore extending through said finger rest.

13. A device as claimed in claim 1 in which said narrow dimension is about one millimeter.

14. A suction device comprising
   (a) a rigid nozzle having a suction passage therethrough and comprising
      (a.1) a suction tip at its distal end and
      (a.2) a connection means at its proximal end, the connection means including
         (a.2.1) a cylindrical body, and
         (a.2.2) a cylindrical end member of smaller diameter than said cylindrical body,
   (b) a rigid handle having a suction bore therethrough connecting to the suction passage, said handle comprising
      (b.1) an end connection whereby it is connectable to a source of suction, and said suction bore comprising
      (b.2) a reception portion and a remainder portion, said reception portion being of larger diameter than said end member and said cylindrical end member being axially received in said reception portion so that there is an annular conduit formed about the end member, said conduit having a small radial thickness and connecting to said remainder portion through a connection port means, and
   (c) a controllable suction port opening into said conduit from the handle exterior upstream of said connection port means.

15. A suction device as claimed in claim 14 wherein the radial thickness of said annular conduit is approximately one millimeter.

16. A suction device as claimed in claim 14 wherein said nozzle and said handle are capable of being separated from one another.

17. A suction device as claimed in claim 16 wherein said handle has a forward opening provided with internal screw threads and said nozzle has a part formed with external screw threads that engage in said internal screw threads.

18. A suction device as claimed in claim 17 comprising engaging means on the nozzle and the handle to limit the rotation of the nozzle.

19. A suction device as claimed in claim 11 in which said nozzle and said handle comprise different materials.

* * * * *